United States Patent [19]

Riley

[11] Patent Number: 5,190,967
[45] Date of Patent: Mar. 2, 1993

[54] MEDICAMENTS FOR TREATING ERECTILE DISORDERS

[75] Inventor: Alan J. Riley, Dunsmore, England

[73] Assignee: Glaxo Group Limited, London, England

[21] Appl. No.: 711,068

[22] Filed: Jun. 4, 1991

[30] Foreign Application Priority Data

Jun. 5, 1990 [GB] United Kingdom ............... 9012469

[51] Int. Cl.$^5$ ............................................. A61K 31/40
[52] U.S. Cl. .................................................... 514/411
[58] Field of Search ......................................... 514/411

[56] References Cited

U.S. PATENT DOCUMENTS

| | | | |
|---|---|---|---|
| 4,659,731 | 4/1987 | Bigg et al. | 514/397 |
| 4,738,979 | 4/1988 | Calderon et al. | 514/396 |
| 4,791,108 | 12/1988 | Clark | 514/233.2 |
| 4,886,798 | 12/1989 | Clark | 514/233.2 |
| 4,956,365 | 9/1990 | Clark et al. | 514/233.2 |
| 4,960,891 | 10/1990 | Clark | 546/48 |

FOREIGN PATENT DOCUMENTS

0439320A1 7/1991 European Pat. Off. .

OTHER PUBLICATIONS

VII World Congress of Psychiatry, Oct. 1989, Program.
Susset et al., *The Journal of Urology*, 141, Jun. 1989.
Riley et al., *Sexual and Marital Therapy*, 4, 1, 1989, 17-26.
Morales et al., *Impotence*, Urologic Clinics of North America, 15, 1, 1988.

*Primary Examiner*—Leonard Schenkman

*Attorney, Agent, or Firm*—Bacon & Thomas

[57] ABSTRACT

The use of a compound of formula I

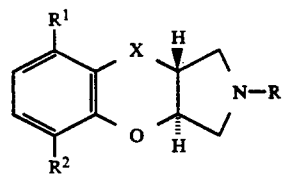

wherein

R is a hydrogen atom or a group selected from $C_{1-6}$alkyl (optionally substituted by $C_{3-7}$ cycloalkyl), $C_{3-6}$ alkenyl, $C_{3-6}$alkynyl, $C_{3-7}$ cycloalkyl, aralkyl (in which the alkyl moiety contains 1-5 carbon atoms) and —CHO;

$R^1$ and $R^2$, which may be the same or different, represent a hydrogen atom, a halogen atom or a group selected from $C_{1-4}$alkyl, $C_{1-4}$alkoxy, hydroxyl, cyano, nitro and —$NR^3R^4$ where $R^3$ and $R^4$ is each a hydrogen atom or a $C_{1-4}$alkyl group and X is an oxygen atom or a group —$CH_2$—; or a physiologically acceptable salt or hydrate thereof for treating, relieving or preventing the effects of sexual dysfunction.

Preferred compounds include trans-5-fluoro-2,3,3a,9a-tetrahydro-1H-[1,4] benzodioxino [2,3-c]pyrrole and trans-5-fluoro-1,2,3,3a,9,9a-hexahydro[1] benzopyrano [2,3-c]pyrrole.

Conditions that may be treated in this manner include, in the case of the male, erectile inadequacy and, in the case of the female, sexual arousal disorder.

4 Claims, No Drawings

MEDICAMENTS FOR TREATING ERECTILE DISORDERS

This invention relates to a new medical use for certain heterocyclic compounds and pharmaceutical compositions containing them. In particular it relates to the use of the benzodioxinopyrrole compounds disclosed in published UK Patent Specification No. 2157691 and physiologically acceptable salts and hydrates thereof and the benzopyranopyrrole compounds disclosed in published UK Patent Specification No. 2182040 and physiologically acceptable salts and hydrates thereof in treating sexual dysfunction.

Compounds which may be represented by the formula (I)

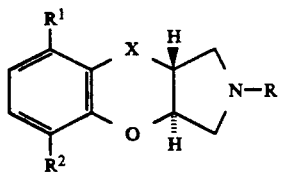

wherein R is a hydrogen atom or a group selected from $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1-5 carbon atoms) and —CHO; $R^1$ and $R^2$, which may be the same or different, represent a hydrogen atom, a halogen atom or a group selected from $C_{1-4}$alkyl, $C_{1-4}$alkoxy, hydroxyl, cyano, nitro and —$NR^3R^4$ where $R^3$ and $R^4$ is each a hydrogen atom or a $C_{1-4}$alkyl group; and X is an oxygen atom or a group —$CH_2$—; and the physiologically acceptable salts and hydrates thereof are disclosed in published UK Patent Specification Nos. 2129795, 2157691, 2182040 and published European Patent Specification No. 162592.

In general formula (I), the alkyl, alkenyl and alkynyl groups represented by R, $R^1$ and R2 may be straight or branched chain groups.

When R contains a —C=C— or —C≡C— linkage this is not directly attached to the nitrogen atom. When R is alkyl it may be, for example, methyl, ethyl or propyl, methyl being preferred. When R is an alkyl group substituted by a $C_{3-7}$ cycloalkyl group it may be, for example, cyclopropyl$C_{1-3}$alkyl such as cyclopropylmethyl. When R is alkenyl it may be, for example, allyl and when R is alkynyl it may be, for example, propynyl. When R is cycloalkyl it may be, for example, cyclopropyl. When R is an aralkyl group it may be, for example phen$C_{1-5}$alkyl, such as benzyl.

The halogen atoms represented by $R^1$ and R2 may be fluorine, chlorine, bromine or iodine atoms. Examples of alkyl and alkoxy groups represented by $R^1$ and R2 are methyl, ethyl, methoxy and ethoxy groups. The group —$NR^3R^4$ may be, for example, an amino, methylamino, ethylamino, dimethylamino or diethylamino group.

Suitable physiologically acceptable salts disclosed are the acid addition salts formed with inorganic acids, for example hydrochlorides, hydrobromides, phosphates and sulphates, and with organic acids, for example citrates, tartrates, acetates, maleates and succinates.

It will be appreciated that each compound of formula (I) is a trans isomer and exists as two enantiomers. The structural formulae herein are to be understood to depict either enantiomer of each compound as well as mixtures, including racemates, even though the precise structure as set out relates only to one enantiomer.

The compounds disclosed in the aforementioned patent specifications are described as selective $\alpha_2$-adrenoreceptor antagonists of interest in the treatment or prevention of migraine, thrombosis, diabetes, obesity, hypertension, constipation, paralytic ileus, senile dementia and in particular for the treatment of depression.

We now find that compounds of formula (I) are also of use in the treatment of sexual dysfunction, such as erectile inadequacy and sexual arousal dysfunction.

According to one aspect of the invention we therefore provide a compound of formula (I) or a physiologically acceptable salt or hydrate thereof for use in treating, relieving or preventing the effects of sexual dysfunction.

In an alternative or further aspect the invention provides a method of treatment of a mammal, including man, suffering from or susceptible to the effects of sexual dysfunction which comprises administering to a mammal in need of such treatment an effective amount of a compound of formula (I) or a physiologically acceptable salt or hydrate thereof.

It will be appreciated that whilst compounds of formula (I) will primarily be of use in the alleviation of established symptoms, prophylaxis is not excluded.

In a further aspect the invention provides a compound of formula (I) or a physiologically acceptable salt or hydrate thereof for use in the manufacture of a medicament for treating, relieving or preventing the effects of sexual dysfunction.

In the present specification, the sexual dysfunction may be of the male or female variety. In the former case, male sexual dysfunction incorporates erectile inadequacy and inhibited male orgasm, with erectile inadequacy being particularly amenable to treatment by the present alpha-2 anatagonists. In the case of female sexual dysfunction, this includes sexual arousal disorder and inhibited female orgasm, with the former being particularly amenable to the present method of treatment.

A preferred compound for use according to the present invention is a compound of formula (II)

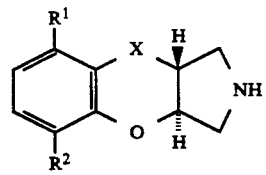

wherein $R^1$ and $R^2$, which may be the same or different, represent a hydrogen atom or a flurine atom, and X is an oxygen atom or a group —$CH_2$—; and its physiologically acceptable salts and hydrates.

Particularly preferred compounds for use according to the present invention are
1. Trans-5-fluoro-2,3,3a,9a-tetrahydro-1H-[1,4]-benzodioxino [2,3-c] pyrrole ($R^1$=F,$R^2$=H,X=O especially in the racemic (±) form. Most preferably, the hydrochloride salt of this compound, particularly in hydrated form, for example as the hemihydrate, is used.
2. Trans-5-fluoro-1,2,3,3a,9,9a-hexahydro [1] benzopyrano [2,3-c] pyrrole ($R^1$=H,$R^2$=F,X=$CH_2$), especially in the racemic (±) form. Most preferably, the hydrochloride salt of this compound is used, either in a hydrated or non-hydrated form.

Compounds for use according to the invention may be administered as the raw material but the active ingredient is preferably presented as a pharmaceutical formulation. The active ingredient may conveniently be presented in unit dose form.

Compounds of formula (I) for use according to the invention may be formulated in a conventional manner using one or more pharmaceutically acceptable carriers or excipients for administration by any convenient route, for example for oral, rectal or parenteral administration. Compounds for use according to the invention may conveniently be formulated for parenteral or preferably oral administration.

For oral administration, the pharmaceutical compositions may take the form of, for example, tablets or capsules prepared by conventional means with pharmaceutically acceptable excipients such as binding agents (for example pregelatinised maize starch, polyvinylpyrrolidone or hydroxypropyl methylcellulose); fillers (for example lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

The compounds for use according to the invention may be formulated for parenteral administration by injection conveniently intravenous or subcutaneous injection, for example by bolus injection or continuous intravenous infusion. Formulations for injection may be presented in unit dosage form, for example, in ampoules or in multi-dose containers, with an added preservative.

The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, for example sterile pyrogen-free water, before use.

Composition for rectal administration may be in the form of suppositories using a conventional suppository excipient.

It will be appreciated that the precise dose administered will depend on the age and condition of the patient, the particular compound used, and the frequency and route of administration. The compounds may be administered in single or divided doses and may be administered one or more times, for example 1 to 4 times, per day.

A proposed daily dose of compounds (I) for administration to man for use according to the invention is 0.01 to 10 mg/kg, for example 0.015 to 3 mg/kg. The daily dose may conveniently be administered in unit dose form, each unit containing for example 0.01 to 3 mg/kg of active ingredient.

The preparation and use of particular α-2-antagonists according to the present invention will now be described by way of example only.

PREPARATION

1)

(±)-trans-5-Fluoro-2,3,3a-9a-tetrahydro-1H-[1,4]-benzodioxino-[2,3-c]pyrrole hydrochloride hemihydrate (A) INTERMEDIATE 1

(±)-(trans)-5-Fluoro-2,3-dihydro-2,3-bis[phenylmethoxy)methyl]1,4-benzodioxin

A mixture of 3-fluorobenzene-1,2-diol (5.12 g) and (R*,R*)-1,4-bis (phenylmethoxy)-2,3-butanediol, bis (4-methylbenzenesulphonate) (24.4 g) was stirred with dimethylformamide (DMF) (160 ml) under a nitrogen stream for 45 min. Anhydrous cesium carbonate (13.0 g) was added and the mixture was heated to 150° under reflux for 18 hours. The dark brown mixture was cooled to 30° and diluted with di-isopropyl ether (370 ml) and water (30 ml). The layers were separated and the aqueous layer was re-extracted with diisopropyl ether (150 ml) and then 100 ml). The extracts were sequentially washed within 1M hydrochloric acid (300 ml), 30% aqueous sodium chloride (100 ml) and were combined and evaporated in vacuo to a dark brown oil (12.6 g) which was dissolved in a light petroleum-dichloromethane (3:1) (40 ml) and chromatography over Sorbsil (Trade Mark) (126 g) using light petroleum-dichloromethane mixtures of gradually increasing polarity. Combination of appropriate fractions and evaporation of the solvents gave the title compound as a yellow oil (7.0 g), NMR (CDCl$_3$) 2.6–2.8 (10H, m, Ph), 3.18–3.38 (3H,m,6-H, 7-H, 8-H), 5.32–5.58 (4H, m C$\underline{H}_2$Ph) 5.64 (2H, m, 2-H, 3-H),6.06–6.32 (4H, m,C$\underline{H}_2$O).

(B) INTERMEDIATE 2

(±)
(trans)-5-Fluoro-2,3-dihydro-1,4-benzodioxin-2,3-dimethanol

Intermediate 1 (7.0 g) was dissolved in a mixture of toluene (70 ml) and anisole (7.8 ml) and the solution was stirred and cooled to −5° under a gentle stream of nitrogen. Anhydrous aluminum chloride (2.4 g) was added and the temperature was maintained at 0°-5° for 20 min. More anhydrous aluminium chloride (2.4 g) was added and after 20 min. at 0.5° the mixture was allowed to warm to 20° with continued stirring. After 20 min. at 20° it was cooled back to 0°, water (25 ml) was added and after 5 min. stirring at 20°, the mixture was diluted with ethyl acetate (75 ml) and the layers were separated. The aqueous (lower) layer was re-extracted with ethyl acetate (2×50 ml) and the organic solutions were washed with 30% aqueous sodium chloride (25 ml) and were combined and concentrated in vacuo to 36 g, giving a thick slurry of slightly purple crystals. After 30 min at 20°, the crystals were harvested, washed with toluene (10 ml), light petroleum (20 ml) and diisopropyl ether (20 ml) and dried to give the title compound (2.93 g) m.p. 122°-124°. Concentration of the mother liquor gave a crude second crop of the title compound (0.32 g) which after chromatographic purification afforded a further quantity of pure title compound 0.24 g, m.p. 121°-123°.

(C) INTERMEDIATE 3

(±)-trans-5-Fluoro-2,3-dihydro-1,4-benzodioxino-2,3-dimethanol, bis methanesulphonate A solution of Intermediate 2 (3.10 g) in dichloromethane (30 ml) and triethylamine (6.4 ml) was stirred for 10 min, with ice-bath cooling. A solution of methanesulphonyl chloride (3.2 ml) in dichloromethane (10 ml) was added during 10 min. and the resultant suspension was stirred for 30 min. Water (25 ml) was added and the mixture was stirred for 20 min. the layers were then separated and the aqueous layer was re-extracted with dichloromethane (25 ml). The organic solutions were washed with water (25 ml), and were combined and evaporated to an oil which was chromatographed over Sorbsil (Trade Mark) (40 g), eluting with 9:1 dichloromethane-ethyl acetate. Appropriate fractions were combined and evaporated to a pale yellow oil (5.9 g) which crystallised slowly from ethyl acetatediisopropyl ether to afford the title compound as prisms (4.15 g) m.p. 65.5°-68.5°.

(D) INTERMEDIATE 4

(±)-trans-5-Fluoro-2,3,3a-9a-tetrahydro-2-(phenylmethyl)-1H-[1,4]-benzodioxino-[2,3-c]-pyrrole A homogenised mixture of phenylmethanamine (8 ml) and Intermediate 3 (5.3 g) was heated to 130° for 15 min. then cooled to 25°. The partly crystalline mixture was partitioned between di-isopropyl ether (80 ml) and water (80 ml). The aqueous layer was re-extracted with di-isopropyl ether (100 ml) and the organic solutions were sequentially washed with 2.5% aqueous acetic acid (2×50 ml) and 15% aqueous sodium chloride (100 ml) containing sodium hydrogen carbonate (5 g). They were then combined and evaporated in vacuo to an orange-brown oil (3.8 g) which crystallised spontaneously. This was crystallised from diisopropyl ether-light petroleum (1:1) to give pink crystals of the title compound as two crops; (1) 1.5 g m.p 79°-81° and (2) 1.4 g m.p. 79°-81°. Chromatography of the mother liquor gave a third crop (0.6 g)

EXAMPLE 1

(±)-trans-5-Fluoro-2,3,3a-9a-tetrahydro-1H-[1,4]-benzodioxino-[2,3-c]-pyrrole hydrochloride hemihydrate A solution of Intermediate 4 (2.3 g) in IMS (110 ml) was stirred under hydrogen at ca. 25° with 5% palladium on charcoal (1.15 g) until uptake ceased (270 ml). The catalyst was filtered off using a kieselguhr pad, the filter was washed through with IMS (3×20 ml) and the combined filtrates were evaporated in vacuo to a pale pink oil (1.6 g). This was re-dissolved in IMS (10 ml) and 10M hydrochloric acid (1 ml) was added. After 30 min. at 20°, the resultant white crystals were harvested, washed with IMS (3 ml), 1:1 IMS-diisopropyl ether (4 ml) and di-isopropyl ether (2×5 ml) to afford the title compound as a hemihydrate (1.09 g) m.p. ca. 245° (sublimes above 210°).

2)
(±)-trans-5-Fluoro-1,2,3,3a-9,9a-hexahydro[1]-benzopyrano-[2,3-c]-pyrrole hydrochloride

INTERMEDIATE 5

4-[(3-Fluoro-2-hydroxyphenyl)carbonyl]-3-hydroxy-2-(5H)-furanone

A solution of 1-(3-fluoro-2-hydroxyphenyl) ethanone (30 g) and diethyl oxalate (31 g) in ethanol (600 mls) was added dropwise to sodium ethoxide (from 9.85 g of sodium) in ethanol (600 mls) and the mixture was stirred and heated at reflux for 2 days. The mixture was cooled, diluted with 60-80 petrol and the solid was collected and dried. A suspension of the product in water (1.2 l) was stirred with formaldehyde (24 mls of 37%) for 1.5 hours. The solid was filtered out, the filtrate was washed with ether, and traces of ether were removed by evaporation under vacuum. The aqueous solution was acidified to pH3, the precipitate was collected, washed with water and recrystallised from acetone/water to give the title compound as yellow needles (18.7 g). M.p. 194°-208° (decomp), i.r. λmax (nujol) 1768, 1642 cm$^{-1}$ (C=O).

INTERMEDIATE 6

5-Fluoro-1H-furo[3,4-b][1]benzopyran-3,9-dione

A solution of Intermediate 5 (24 g) in acetic acid (200 mls) and concentrated hydrochloric acid (40 mls) was heated at reflux for 1 hour. The mixture was allowed to cool, and was concentrated to a volume of 100 mls. Water was added, the precipitate solid was collected, washed with water and dried to yield the title compound. M.p. 164°.

INTERMEDIATE 7

Cis-(±)-5-Fluoro-9,9a-dihydro-1H-furo[3,4-b][1]benzopyran-3(3aH)-one

Intermediate 6 (23 g) in 1,4-dioxan (500 mls) was hydrogenated for 5 days over 10% palladium on carbon (3 g). Acetic acid (10 mls) and a further 0.8 g of catalyst were added, and hydrogenation was continued for a further 23 hours. The catalyst was filtered off, washed with ethyl acetate and the filtrate was concentrated to a volume of 150 mls. The suspension was filtered, the filtrate was evaporated to dryness, and the resulting gum was purified by chromatography eluting with dichloromethane to give the title compound as a white solid. M.p. 75.5°-77.5°.

INTERMEDIATE 8 trans-(±)-8-Fluoro-3,4-dihydro-3-(hydroxymethyl)-2H-1-benzopyran-2-carboxylic acid methyl ester.

A mixture of Intermediate 7 (2 g) and dried potassium carbonate (3.9 g) in dry methanol (20 mls) was stirred under nitrogen for 23 hours. Wet ethyl acetate was added, and the mixture was stirred for 20 minutes. Further quantities of ethyl acetate and water were added, the ethyl acetate layer was separated, washed with water, dried and the solvent was evaporated. The resulting oil (0.58 g) was purified by chromatography eluting with dichloromethane-methanol (15:1) to yield the title compound as an oil. NMR (CDCl$_3$) δ 7.0-6.72 (3H, m, aromatic), 4.96 (1H, d, 2-H), 3.87 (3H, s, methyl ester), 3.67 (2H, d, CH$_2$O-), 2.9-2.5(3H, m, 3-H, 4-H$_2$), 2.15 (1H, Br, OH).

INTERMEDIATE 9 trans-(±)-8-Fluoro-3,4-dihydro-2H-1-benzopyran-2,3-dimethanol

A solution of Intermediate 8 (2.2 g) in dry THF (30 mls) was added dropwise to a stirred suspension of lithium aluminium hydride (0.46 g) in THF (30 mls) at 0°–5°. After 1 hour, saturated ammonium chloride solution (10 mls) was added, the solid was filtered off and washed with THF. Evaporation of the combined solutions yielded a gum which was partitioned between ethyl acetate and water. The aqueous layer was evaporated to dryness, the residue was extracted with ethyl acetate and the combined ethyl acetate layers were dried and the solvent was evaporated. A solution of the product in a small volume of ethyl acetate was diluted with petrol until no more solid precipitated. The solid was collected and dried to yield the title compound (1.5 g), M.p. 111°.

INTERMEDIATE 10 trans-(±)-8-Fluoro-3,4-dihydro-2H-1-benzopyran-2,3-dimethanol, bis (methanesulphonate)

Methanesulphonyl chloride (1.4 g) was added dropwise to a stirred suspension of Intermediate 9 (1.4 g) in dichloromethane containing triethylamine (1.6 g) at 0°–5°. After 1.5 hours the mixture was washed with 2M hydrochloric acid, the acid layer was extracted with dichloromethane, and the combined organic solutions were dried (phase separating paper) and evaporated to dryness. The residue was purified by column chromatography eluting with dichloromethane-methanol (20:1) to yield the title compound as a gum (2.4 g). NMR (CDCl$_3$) δ 7.0–6.75 (3H, m, aromatics), 4.54 (2H, d, 2-C$\underline{H}_2$O), 4.42–4.22 (3H, m, 3-C$\underline{H}_2$O, 2-H), 3.10, 3.05 (6H, s, s, CH$_3$), 3.02–2.76 (2H, m, 4-H$_2$), 2.53 (1H, m, 3-H).

INTERMEDIATE 11 trans-(±)-5-Fluoro-1,2,3,3a,9,9a-hexahydro-2-(phenylmethyl)-[1]benzo- pyrano[2,3-c]pyrrole, hydrochloride A mixture of benzylamine (6.7 g) and Intermediate 10 (2.3 g) was stirred and heated to 120° under nitrogen for 50 minutes. After cooling, the mixture was partitioned between ethyl acetate and 2M sodium hydroxide solution, the layers were separated and the aqueous layer was further extracted with ethyl acetate. The combined organic solutions were washed with brine and then shaken with 2M hydrochloric acid. The precipitated solid was collected, washed with water and ethyl acetate, and dried to give the title compound as a white powder (1.3 g). M.p. 210°–212°. NMR (DMSOd$_6$) δ 12.28, 12.00 (1H, 2xBr S, NH+), 7.8–7.6, 7.6–7.4 (5H, m, Ph), 7.2–6.85(3H, m, 7-H, 6-H, 8-H), 4.65–4.1(3H, m, C$\underline{H}_2$Ph, 3a-H), 3.9–2.25 (7H, m, 1-H$_2$, 3-H$_2$, 9-H$_2$ 9a-H).

EXAMPLE 2 trans-(±)-5-Fluoro-1,2,3,3a,9,9a-hexahydro[1]benzopyrano[2,3-c]pyrrole hydrochloride A solution of Intermediate 11 (1.2 g) in methanol (50 mls) was hydrogenated over 10% palladium on charcoal (0.2 g) for 17 hours. The catalyst was filtered off, and the filtrate was evaporated to dryness. Crystallisation of the resulting solid from isopropyl alcohol/methanol gave the title compound (0.63 g). M.p. 259°. NMR (DMSOd$_6$) δ9.9 (2H, Br S, NH$_2$+), 7.2–6.85 (3H, m, aromatic), 4.24 (1H, d of t, 3a-H), 3.8–2.78 (6H, m, 1-H$_2$, 3-H$_2$, 9-H$_2$), 2.27 (1H, m, 9a-H).

PHARMACEUTICAL EXAMPLES

In the following examples, 'Active Ingredient' refers to either (±) trans-5-fluoro-2,3,3a,9a-tetrahydro[1,4-]benzodioxino[2,3-c]pyrrole hydrochloride or (±)-trans-5-fluoro-1,2,3,3a,9,9a-hexahydro[1] benzopyrano [2,3-c]pyrrole hydrochloride. Other compounds of the invention may be formulated in similar fashion.

| 1. Oral Capsule | |
| --- | --- |
| | per capsule |
| Active Ingredient | 50 mg |
| Magnesium stearate | 0.5 mg |
| Anhydrous lactose | 50 mg |

Blend the active ingredient with the lactose and magnesium stearate. Fill the blend into appropriate size hard gelatin capsules (lock fitting type) on an automatic capsule filling machine.

| 2. Oral Syrup | |
| --- | --- |
| | per 5 ml dose |
| Active Ingredient | 50 mg |
| Sodium citrate | 25 mg |
| Citric acid | to pH 4.5 |
| Sunset yellow FCF (Dye) | 0.25 mg |
| Methyl hydroxybenzoate sodium | 5.0 mg |
| Propyl hydroxybenzoate sodium | 2.0 mg |
| Liquid orange flavour | qS |
| Sucrose | 3.25 g |
| Purified water | to 5.0 ml |

Dissolve the sucrose in a minimum quantity of water. Add a concentrated solution of sodium citrate with stirring and adjust the pH to 4.5 with citric acid. With continued stirring, add a 10% aqueous solution of the active ingredient, followed by a solution of the dye, a solution of the hydroxybenzoates and lastly the flavour. Adjust almost to volume with water and stir. Check the pH and adjust to 4.5 with citric acid if necessary. Make up to volume with water.

| 3. Oral Tablet | |
| --- | --- |
| | per tablet |
| Active Ingredient | 50 mg |
| Polyvinylpyrrolidone | 4.0 mg |
| Sodium starch glycollate | 10.0 mg |
| Magnesium stearate | 2.0 mg |
| Lactose to tablet core weight to | 200 mg |

Blend the active ingredient with the lactose. Add a sufficient quantity of polyvinylpyrrolidone solution to produce a damp mass suitable for granulation. Prepare the granules and dry using a tray or fluid bed dryer. Pass through a sieve, blend with the remaining ingredients and compress into 8 mm diameter tablets on a tablet machine. Film coat the tablet cores with hydroxypropyl methyl cellulose or similar film forming material, using either an aqueous or non-aqueous solvent system. A plasticizer and suitable colour may be included in the film coating solution.

CLINICAL TRIALS

The efficacy of the compound of Example 1 in the treatment of Secondary Male Erectile Disorder was determined in a randomised, double-blind, placebo-controlled, cross-over study. Patients entered a placebo run-in for 1 week and those eligible were then randomised into either Example 1 compound 8 mg bd or matching placebo for 2 weeks. After a 2 week washout patients were crossed-over onto the next treatment. The efficacy measures used were successful intercourse; median and maximum sexual interest and the presence of spontaneous erections.

Patients were more likely to attempt intercourse when taking the compounds of Example 1 than when taking placebo. The odds ratio for successful intercourse on Example 1 compound compared with placebo was 3:1 (95% confidence limits 0.5-17.3). Maximum sexual interest showed a significant difference between treatments (p=0.014); patients on Example 1 compound had an average increase in maximum sexual interest of 16% over placebo (95% confidence limits 4.5%-27.8%). The proportion of patients with spontaneous erections appeared to be greater in the Example 1 compound group but was of borderline significance (p=0.06).

What is claimed is:

1. A method of treatment of a mammal, including man, suffering from or susceptible to the effects of male erectile disorder which comprises administering to a mammal in need of such treatment an effective amount of a compound of formula (I):

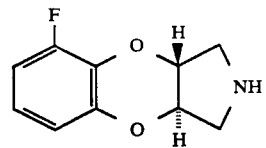

or a physiologically acceptable salt or hydrate thereof.

2. A method of treatment according to claim 1 which comprises administering to a mammal in need of such treatment an effective amount of (±)-trans-5-fluoro-2,3,3a,9a-tetrahydro-1H-[1,4]-benzodioxino[2,3-c]pyrrole hydrochloride.

3. A method of treatment according to claim 2 which comprises administering to a mammal in need of such treatment an effective amount of (±)-trans-5-fluoro-2,3,3a,9a-tetrahydro-1H-[1,4]-benzodioxino[2,3-c]pyrrole hydrochloride hemihydrate.

4. A method of treatment of a mammal, including man, suffering from the effects of male erectile disorder which comprises administering to a mammal in need of such treatment an effective amount of a compound of formula (I):

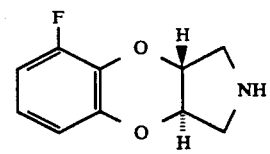

or a physiologically acceptable salt or hydrate thereof.

* * * * *